(12) United States Patent
Sawayama

(10) Patent No.: US 9,153,046 B2
(45) Date of Patent: Oct. 6, 2015

(54) ULTRASONIC DIAGNOSTIC APPARATUS, METHOD, AND PROGRAM COMBINING STRUCTURAL AND ELASTICITY IMAGES

(75) Inventor: Yuki Sawayama, Tokyo (JP)

(73) Assignee: HITACHI MEDICAL CORPORATION, Tokyo (JP)

(*) Notice: Subject to any disclaimer, the term of this patent is extended or adjusted under 35 U.S.C. 154(b) by 205 days.

(21) Appl. No.: 13/823,037

(22) PCT Filed: Sep. 11, 2011

(86) PCT No.: PCT/JP2011/070658
§ 371 (c)(1),
(2), (4) Date: Mar. 13, 2013

(87) PCT Pub. No.: WO2012/043200
PCT Pub. Date: Apr. 5, 2012

(65) Prior Publication Data
US 2013/0169632 A1 Jul. 4, 2013

(30) Foreign Application Priority Data

Sep. 29, 2010 (JP) ................................. 2010-219516

(51) Int. Cl.
*G06T 11/00* (2006.01)
*G06T 15/00* (2011.01)
(Continued)

(52) U.S. Cl.
CPC ............... *G06T 11/003* (2013.01); *A61B 8/085* (2013.01); *A61B 8/463* (2013.01); *A61B 8/466* (2013.01); *A61B 8/467* (2013.01); *A61B 8/483* (2013.01); *A61B 8/485* (2013.01); *A61B 8/5246* (2013.01); *G01S 7/52042* (2013.01);
(Continued)

(58) Field of Classification Search
USPC ....................................................... 345/419
See application file for complete search history.

(56) References Cited

U.S. PATENT DOCUMENTS 5,720,291 A 2/1998 Schwartz
6,413,219 B1 7/2002 Avila et al.
(Continued)

FOREIGN PATENT DOCUMENTS

CN 101427931 A 5/2009
EP 1 554 982 A1 7/2005
(Continued)

OTHER PUBLICATIONS

J. Lindop et al., "3D Elastography Using Freehand Ultrasound", 2006, Ultrasound in Med. & Biol., vol. 32, No. 4, pp. 529-545.*
(Continued)

*Primary Examiner* — Kee M Tung
*Assistant Examiner* — Grace Q Li
(74) *Attorney, Agent, or Firm* — Oliff PLC

(57) ABSTRACT

A sectional image and a two-dimensional elasticity image on an arbitrary cross section are added at a first combination ratio received from an operator to produce an arbitrary cross-section combined image. A three-dimensional image and a three-dimensional elasticity image of a predetermined part are added at a second combination ratio received from the operator to produce a three-dimensional combined image. The arbitrary cross-section combined image and the three-dimensional combined image are displayed side by side in a display. This can provide an ultrasonic diagnostic apparatus capable of facilitating the grasp of the structure and the recognition of the hardness of the living organ within the object from the plurality of images.

8 Claims, 10 Drawing Sheets

(51) Int. Cl.
*G01S 15/89* (2006.01)
*G01S 7/52* (2006.01)
*A61B 8/08* (2006.01)
*A61B 8/00* (2006.01)

(52) U.S. Cl.
CPC ........ *G01S 7/52071* (2013.01); *G01S 7/52073* (2013.01); *G01S 7/52074* (2013.01); *G06T 15/00* (2013.01); *G01S 15/8993* (2013.01)

(56) References Cited

U.S. PATENT DOCUMENTS

| | | | |
|---|---|---|---|
| 6,558,324 | B1 | 5/2003 | Von Behren et al. |
| 2006/0052702 | A1 | 3/2006 | Matsumura et al. |
| 2007/0055161 | A1* | 3/2007 | Garg et al. .................... 600/458 |
| 2008/0071174 | A1* | 3/2008 | Waki et al. .................... 600/442 |
| 2011/0160590 | A1 | 6/2011 | Waki et al. |

FOREIGN PATENT DOCUMENTS

| | | |
|---|---|---|
| EP | 1 815 796 A1 | 8/2007 |
| JP | A-9-262236 | 10/1997 |
| JP | A-2004-135929 | 5/2004 |
| JP | A-2006-130071 | 5/2006 |
| JP | A-2006-212166 | 8/2006 |
| JP | A-2007-514477 | 6/2007 |
| JP | A-2008-259605 | 10/2008 |
| WO | WO 2010/024023 A1 | 3/2010 |

OTHER PUBLICATIONS

Translation of Office Action issued in Chinese Patent Application No. 201180046493.7 dated Jun. 30, 2014.

Dec. 13, 2011 International Search Report issued in International Application No. PCT/JP2011/070658.

Extended European Search Report issued in European Patent Application No. 11828761.4 dated May 15, 2014.

* cited by examiner

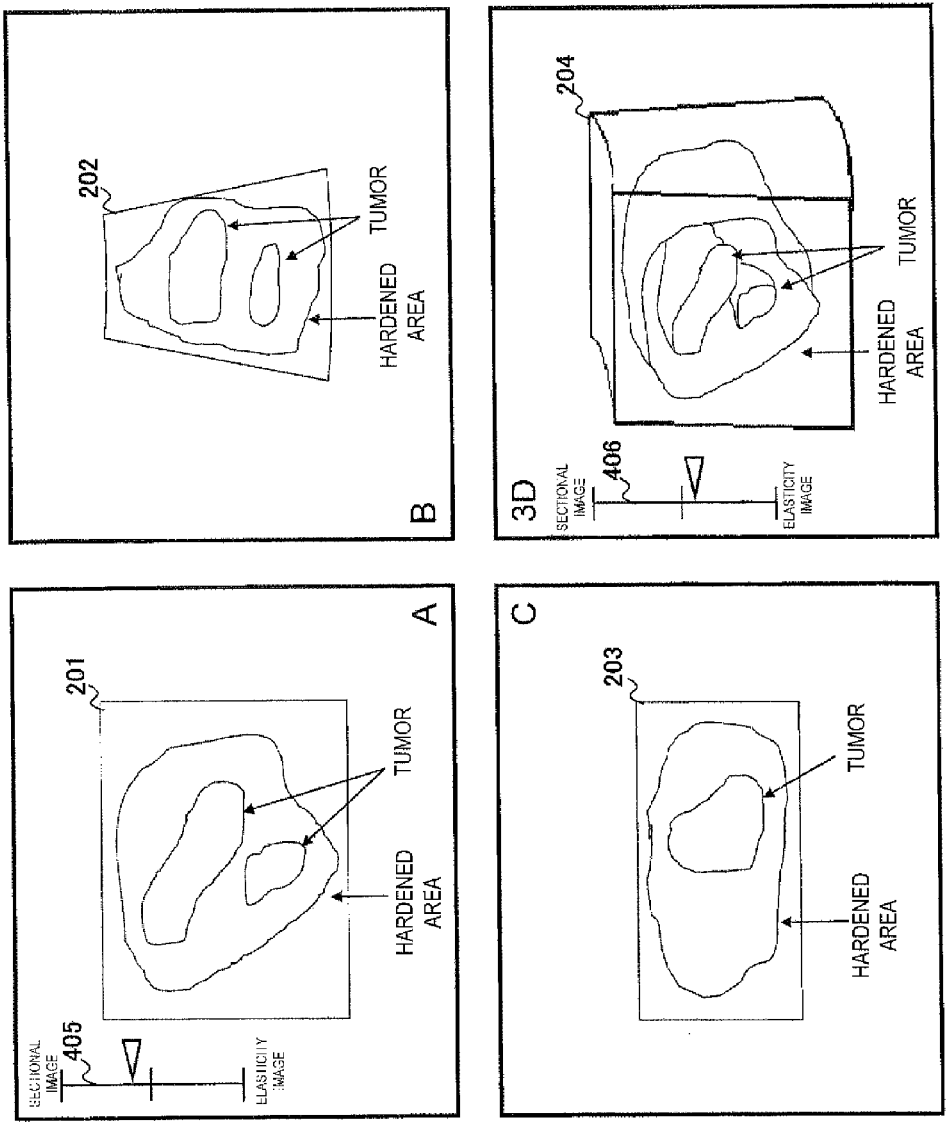

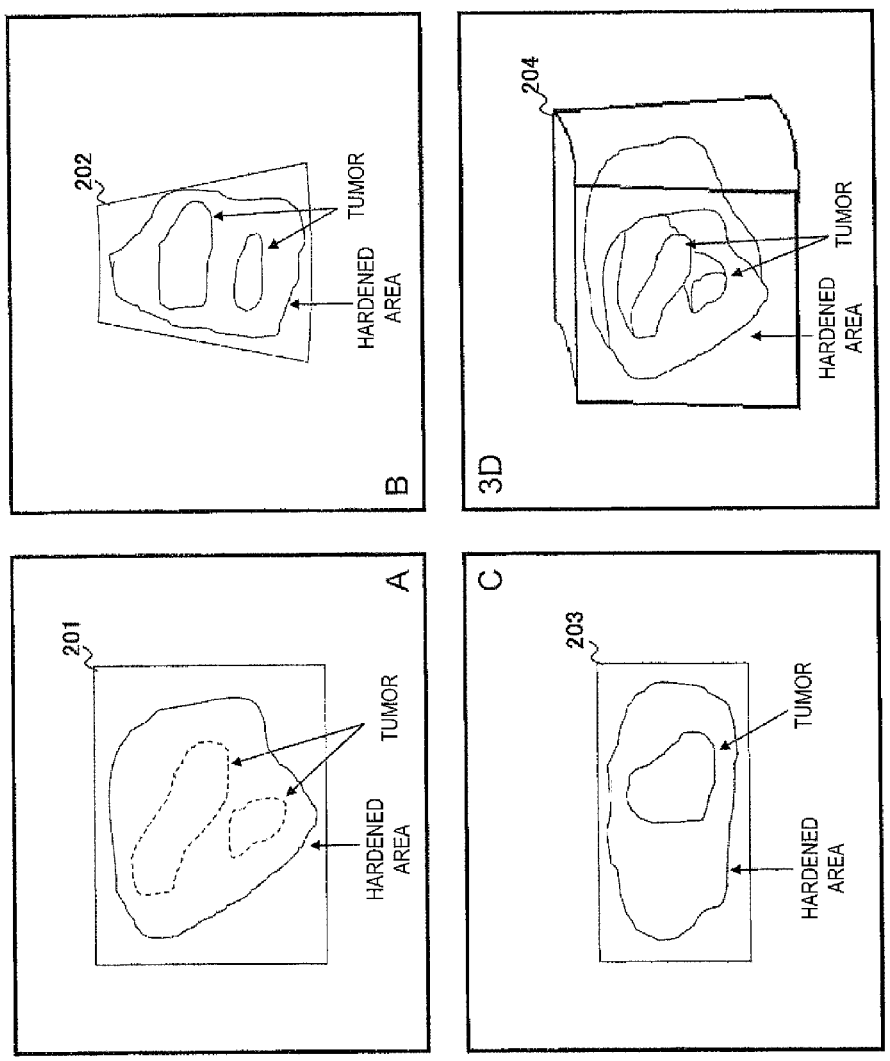

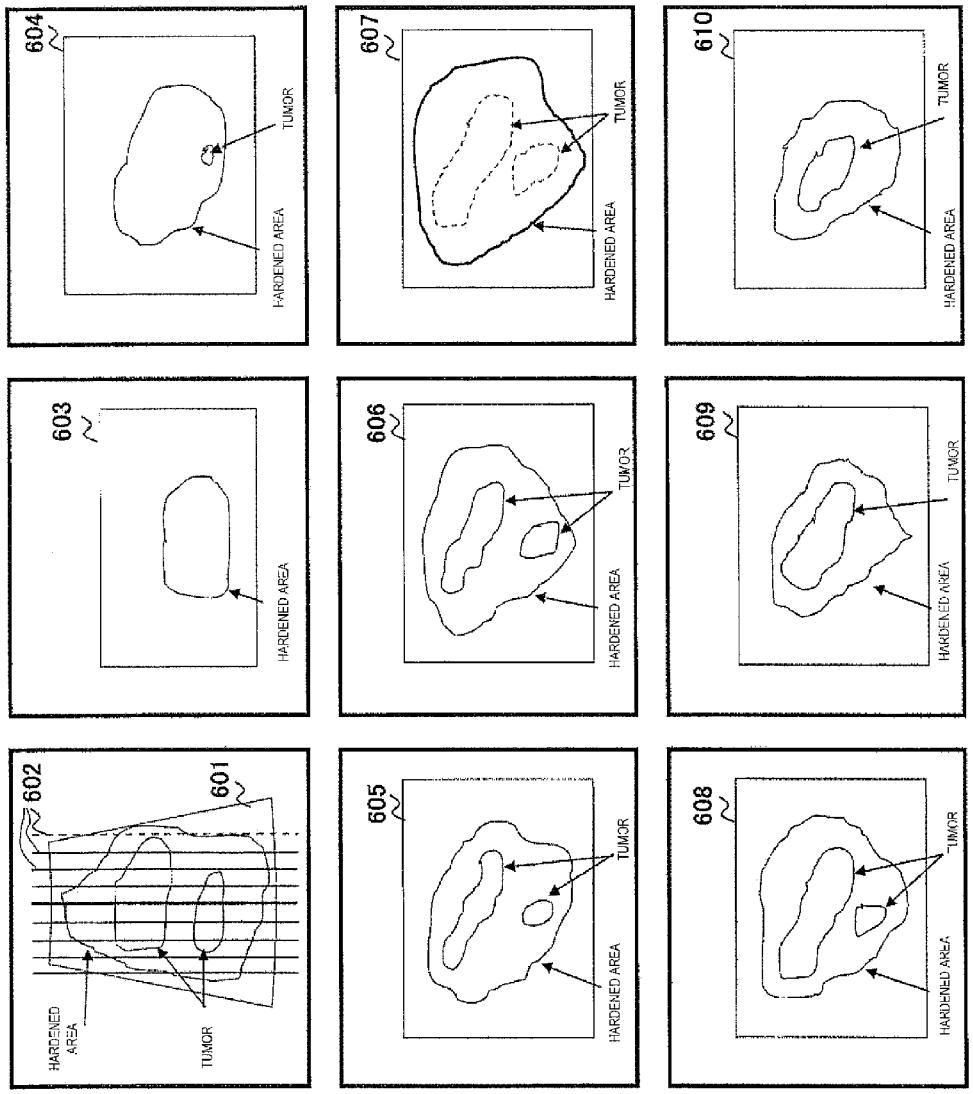

ULTRASONIC DIAGNOSTIC APPARATUS, METHOD, AND PROGRAM COMBINING STRUCTURAL AND ELASTICITY IMAGES

TECHNICAL FIELD

The present invention relates to an ultrasonic diagnostic apparatus which displays an ultrasonic image of a part to be diagnosed within an object using ultrasonic, and more particularly, to an ultrasonic diagnostic apparatus capable of displaying a sectional image of the object and a three-dimensional elasticity image representing the hardness of a living organ of the object.

BACKGROUND ART

An ultrasonic diagnostic apparatus can transmit ultrasonic into an object, receive the ultrasonic reflection echo signal of a living organ from the reflected wave, and perform signal processing on the signal to produce a monochrome sectional image of a part to be diagnosed having intensities as the ultrasonic reflectivities as described in Patent Literature 1. Three-dimensional volume data can be produced from a plurality of such monochrome sectional images and rendered to produce and display a monochrome three-dimensional image. Patent Literature 1 has also disclosed a technique of providing a two-dimensional elasticity image and a three-dimensional elasticity image in which an elasticity value (such as strain and coefficient of elasticity) representing the hardness of the part to be diagnosed is represented by a hue.

Patent Literature 2 has disclosed a technique in which a monochrome three-dimensional image is produced such that a harder organ is shown more opaquely and a softer organ is shown more transparently to allow intuitive recognition of the shape and the volume of a hard part or a soft part when a three-dimensional elasticity image is displayed over the monochrome three-dimensional image. Patent Literature 2 has also disclosed a method in which an arbitrary cross section is taken from three-dimensional volume data of monochrome sectional images to produce and display the monochrome sectional image of the arbitrary cross section.

Patent Literature 3 has disclosed a technology in which a monochrome sectional image is added to a two-dimensional elasticity image at a set ratio to produce and display a combined image, and structure information and elasticity information of an organ are obtained from a single image.

PRIOR ART REFERENCES

Patent Literature

Patent Literature 1: JP-A-2008-259605
Patent Literature 2: U.S. Pat. No. 6,413,219
Patent Literature 3: JP-A-2004-135929

SUMMARY OF THE INVENTION

Problems that the Invention is to Solve

In the image provided by superimposing the monochrome three-dimensional image on the three-dimensional elasticity image at the appropriate ratio, three-dimensional structure information and elasticity information in the part to be diagnosed can be recognized at the same time. In the image provided by superimposing the monochrome sectional image of the arbitrary cross section on the two-dimensional elasticity image, two-dimensional structure information and elasticity information of the arbitrary cross section can be recognized at the same time. If the combined image of the monochrome three-dimensional image and the three-dimensional elasticity image and the combine image of the monochrome sectional image of the arbitrary cross section and the two-dimensional elasticity image can be displayed side by side at the same time, an operator can see the three-dimensional combined image to understand the overview and can see the combined image of the arbitrary cross section to grasp the internal structure and elasticity information of the region of interest.

It is necessary to superimpose the monochrome three-dimensional image on the three-dimensional elasticity image at the appropriate ratio to allow the recognition of both the images. This also applies to the combination ratio of the monochrome sectional image of the arbitrary cross section and the two-dimensional elasticity image. Since the three-dimensional image is constituted in a different manner from that for the sectional image, the combination ratio appropriate for the three-dimensional image is different from the combination ratio appropriate for the elasticity image.

It is an object of the present invention to provide an ultrasonic diagnostic apparatus capable of displaying a plurality of types of combined images side by side to allow an operator to see the structure within an object and the elasticity of a living organ.

Means for Solving the Problems

To achieve the above object, according to a first aspect, the present invention provides an ultrasonic diagnostic apparatus as described below. Specifically, the ultrasonic diagnostic apparatus includes a sectional image constituting unit which transmits ultrasonic into an object and produces a sectional image of an arbitrary cross section of the object based on a received signal, a two-dimensional elasticity image constituting unit which processes the signal to produce a two-dimensional elasticity image of an elasticity value representing elasticity on the arbitrary cross section, a three-dimensional image producing unit which processes the signal to produce a three-dimensional image of a predetermined part of the object, and a three-dimensional elasticity image producing unit which process the signal to produce a three-dimensional elasticity image of the elasticity value of the predetermined part of the object, an arbitrary cross-section combined image producing unit which adds the sectional image and the two-dimensional elasticity image of the arbitrary cross section at a first combination ratio to produce an arbitrary cross-section combined image, a three-dimensional combined image producing unit which adds the three-dimensional image and the three-dimensional elasticity image of the predetermined part at a second combination ratio to produce a three-dimensional combined image, a display control unit which displays the arbitrary cross-section combined image and the three-dimensional combined image side by side, and an operation unit which receives setting of the first combination ratio and setting of the second combination ratio from an operator.

The operation unit can be used to set the received first combination ratio and the received second combination ratio in the arbitrary cross-section combined image producing unit and the three-dimensional combined image producing unit, respectively. The display control unit can display an indicator representing the first combination ratio and an indicator representing the second combination ratio in the arbitrary cross-section combined image and the three-dimensional combined image, respectively. When the operation unit receives a change of one of the first combination ratio and the second combination ratio, the operation unit can change the other combination ratio in synchronization.

The arbitrary cross-section combined image producing unit can produce the arbitrary cross-section combined image for a plurality of arbitrary cross sections, and in this case, the operation unit can receive setting of the first combined ratio for each of the plurality of arbitrary cross sections, and the arbitrary cross-section combined image producing unit can produce the combined image at the first combination ratio set for each of the plurality of arbitrary cross sections. The operation unit can receive a selection of one or more images of the arbitrary cross-section combined images of the plurality of cross sections and a change of the combination ratio of the selected arbitrary cross-section combined image from the operator, and in this case, the arbitrary cross-section combined image producing unit can produce the selected arbitrary cross-section combined image with the changed combination ratio.

According to a second aspect, the present invention provides an ultrasonic diagnostic apparatus as described below. Specifically, the ultrasonic diagnostic apparatus includes a sectional image constituting unit which produces a sectional image for a plurality of arbitrary cross sections of an object, a two-dimensional elasticity image constituting unit which processes a signal to produce a two-dimensional elasticity image of an elasticity value representing elasticity on the plurality of arbitrary cross sections, an arbitrary cross-section combined image producing unit which adds the sectional image and the two-dimensional elasticity image of each of the plurality of arbitrary cross sections at a set combination ratio to produce an arbitrary cross-section combined image, a display control unit which displays the arbitrary cross-section combined images of the plurality of arbitrary cross sections in order, and an operation unit which receives setting of the combination ratio for each of the plurality of arbitrary cross sections.

According to a third aspect, the present invention provides an ultrasonic image display method as described below. Specifically, the method includes the steps of transmitting ultrasonic into an object and producing a sectional image of an arbitrary cross section of the object based on a received signal, processing the signal to produce a two-dimensional elasticity image of an elasticity value representing elasticity on the arbitrary cross section, processing the signal to produce a three-dimensional image of a predetermined part of the object, processing the signal to produce a three-dimensional elasticity image of the elasticity value of the predetermined part of the object, adding the sectional image and the two-dimensional elasticity image of the arbitrary cross section at a first combination ratio received from an operator to produce an arbitrary cross-section combined image, adding the three-dimensional image and the three-dimensional elasticity image of the predetermined part at a second combination ratio received from the operator to produce a three-dimensional combined image, and displaying the arbitrary cross-section combined image and the three-dimensional combined image side by side in a display.

According to a fourth aspect, the present invention provides an ultrasonic image display program as described below. Specifically, the program causes a computer to perform the steps of transmitting ultrasonic into an object and producing a sectional image of an arbitrary cross section of the object based on a received signal, processing the signal to produce a two-dimensional elasticity image of an elasticity value representing elasticity on the arbitrary cross section, processing the signal to produce a three-dimensional image of a predetermined part of the object, processing the signal to produce a three-dimensional elasticity image of the elasticity value of the predetermined part of the object, adding the sectional image and the two-dimensional elasticity image of the arbitrary cross section at a first combination ratio received from an operator to produce an arbitrary cross-section combined image, adding the three-dimensional image and the three-dimensional elasticity image of the predetermined part at a second combination ratio received from the operator to produce a three-dimensional combined image, and displaying the arbitrary cross-section combined image and the three-dimensional combined image side by side in a display.

Advantage of the Invention

According to the present invention, the combination ratio of the sectional image and the two-dimensional elasticity image can be set for each image to simultaneously display the plurality of images combined with the optimal setting to facilitate the grasp of the structure and the recognition of the hardness of the living organ within the object from the plurality of images. This leads to an efficient diagnosis.

BRIEF DESCRIPTION OF THE DRAWINGS

FIG. 8 An explanatory view showing an example of combined images in Embodiment 2.

FIG. 9 An explanatory view showing an example of combined images in Embodiment 3.

FIG. 10 An explanatory view showing an example of combined images in Embodiment 4.

BEST MODE FOR CARRYING OUT THE INVENTION

An ultrasonic diagnostic apparatus according to an embodiment of the present invention will hereinafter be described with reference to the accompanying drawings.

Embodiment 1

In the present embodiment, a B mode image representing the distribution of ultrasonic reflectivities of organs in a predetermined cross section of an object is referred to as a monochrome sectional image, a two-dimensional projection image provided by rendering volume data formed of the data of the monochrome sectional image is referred to as a three-dimensional image, an image representing the two-dimensional distribution of elasticity values indicating the elasticity of organs of the object in a predetermined cross section is referred to as a two-dimensional elasticity image, and a two-dimensional projection image provided by rendering volume data formed of the data of the two-dimensional elasticity image is referred to as a three-dimensional elasticity image.

Figure 1:
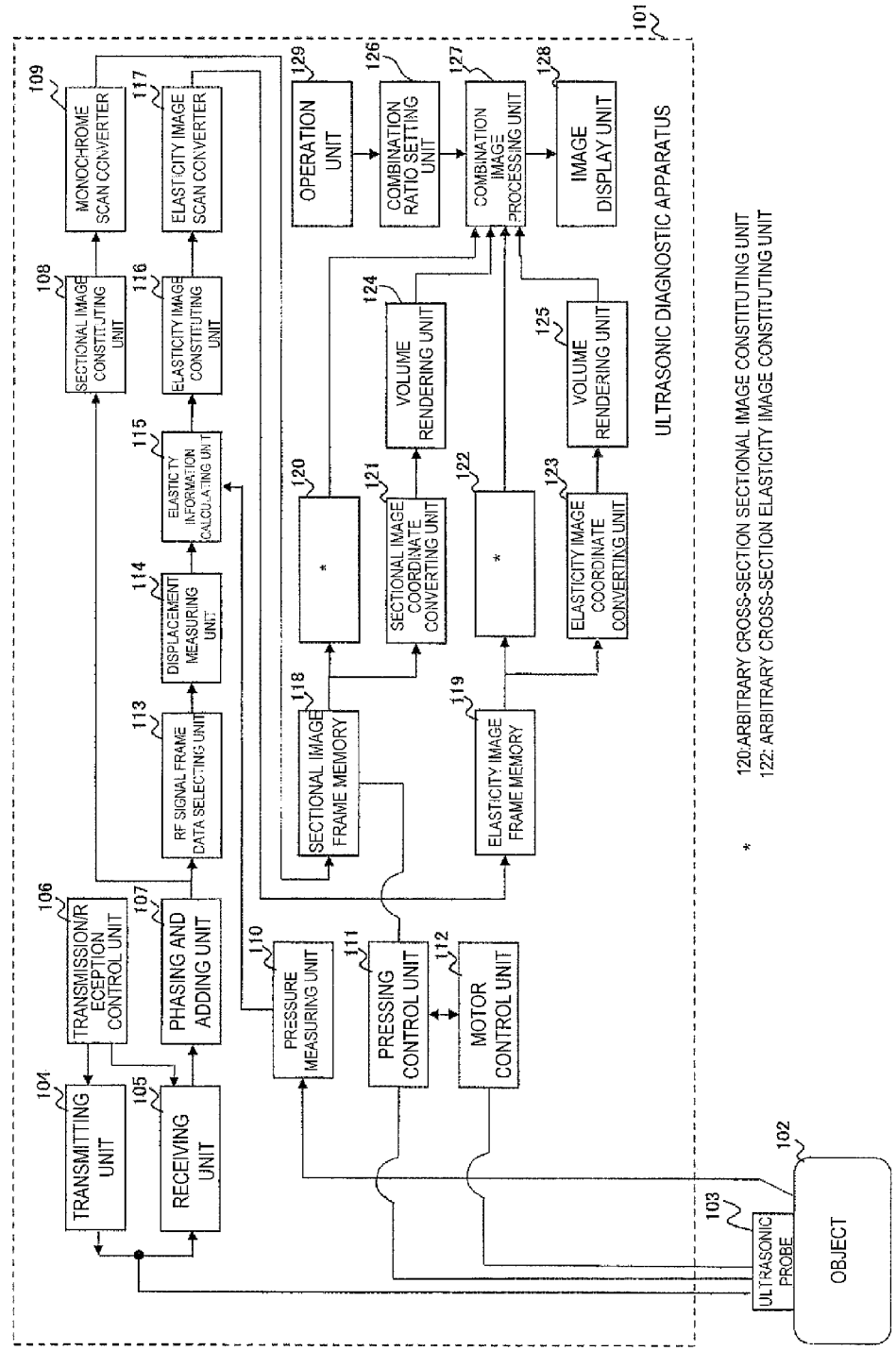
FIG. 1 A block diagram showing the overall configuration of an ultrasonic diagnosis apparatus according to the present invention.

FIG. 1 is a block diagram showing the configuration of the ultrasonic diagnostic apparatus according to Embodiment 1 of the present invention. As shown in FIG. 1, the ultrasonic diagnostic apparatus 101 includes an ultrasonic probe 103 which is brought into contact with an object 102 for use, a transmitting unit 104 which repeatedly transmits ultrasonic at predetermined time intervals to the object through the ultrasonic probe 103, a receiving unit 105 which receives a reflection echo signal provided by the object on the time series, a transmission/reception control unit 106 which controls the transmitting unit and the receiving unit, a phasing and adding unit 107 which phases and adds the reflection echo received in the receiving unit, a pressure measuring unit 110, a pressing control unit 111, and a motor control unit 112.

The probe 103 includes a plurality of oscillators arranged in line or in fan form in a long axis direction, a motor mechanically scanning the plurality of oscillators in a direction (short axis direction) orthogonal to the arrangement direction of the oscillators, a pressing mechanism moving the oscillators upward and downward on the surface of the object 102 to automatically press the object 102, and a pressure sensor. The motor is controlled by the motor control unit 112. The pressing mechanism is controlled by the pressing control unit 111. The output from the pressure sensor is measured by the pressure measuring unit 110.

The probe 103 causes the oscillators to transmit and receives ultrasonic to and from the object 102 while moving the oscillators in the short axis direction by the motor under control of the motor control unit 112, so that the probe 103 can three-dimensionally scan the object 102 with the ultrasonic to collect data. The pressing mechanism can move the oscillators upward and downward under control of the pressing control unit 111 to transmit and receive the ultrasonic while pressurizing the object 102, thereby obtaining elasticity information of the object through processing described later. The pressure applied to the object 102 with the pressing is detected by the pressure sensor and the output therefrom is measured by the pressure measuring unit 110. The motor control unit 112 is controlled to remain at rest during the pressurization by the pressing control unit 111.

The probe 103 may be provided by using a two-dimensional array including not only the plurality of oscillators arranged in the long axis direction but also a plurality of oscillators (1 to k channels) arranged in lines in the short axis direction on an ultrasonic transmission/reception plane to transmit and receive the ultrasonic three-dimensionally without mechanically vibrating the oscillators with the motor. Alternatively, an operator may manually move the probe 103 in the short axis direction to transmit and receive the ultrasonic three-dimensionally. In addition, when the ultrasonic probe 103 employs the two-dimensional array, three-dimensionally ultrasonic data may be collected by scanning of the ultrasonic beam in the short axis direction along the curvature of the ultrasonic transmission/reception plane or the short axis direction produced through electron focus.

The transmitting unit 104 has the functions of producing a transmission wave pulse for driving the ultrasonic probe 103 to generate the ultrasonic and setting the convergence point of the ultrasonic to be transmitted at a certain depth. The receiving unit 105 amplifies the reflection echo signal received by the ultrasonic probe 103 with a predetermined gain to produce an RF signal, that is, a reception wave signal. The phasing and adding unit 107 receives the RF signal amplified by the receiving unit 105 to control the phase thereof and forms the ultrasonic beam for a single or a plurality of convergence points to produce RF signal frame data.

The ultrasonic diagnostic apparatus 101 includes, as components for producing a monochrome sectional image of a part to be diagnosed having intensities as ultrasonic reflectivities from RF frame data and a three-dimensional image, a sectional image constituting unit 108, a monochrome scan converter 109, a sectional image frame memory 118, a sectional image coordinate converting unit 121, a volume rendering unit 124, and an arbitrary cross-section sectional image constituting unit 120. In addition, the ultrasonic diagnostic apparatus 101 includes, as components for producing a two-dimensional elasticity image from the RF signal frame data and a three-dimensional elasticity image, an RF signal frame data selecting unit 113, a displacement measuring unit 114, an elasticity information calculating unit 115, an elasticity image constituting unit 116, an elasticity image scan converter 117, an elasticity image frame memory 119, an elasticity image coordinate converting unit 123, a volume rendering unit 125, and an arbitrary cross-section elasticity image constituting unit 122.

The ultrasonic diagnostic apparatus also includes an operation unit 129 which receives setting from the operator, a combination ratio setting unit 126 which is used to set a combination ratio in producing a combined image set by the operator, a combined image processing unit 127 which produces the combined image at the set combination ratio, and an image displaying unit 128.

The sectional image constituting unit 108 receives the RF signal frame data from the phasing and adding unit 107 and performs signal processing such as gain correction, log compression, detection, outline enhancement, and filtering to obtain sectional image frame data. The monochrome scan converter 109 is formed of a coordinate converter, a frame memory which stores a plurality of converted sectional image frame data on the time series, and a controller. The monochrome scan converter 109 obtains the sectional image frame data within the object stored in the frame memory as a single image, reads the obtained sectional image frame data in synchronization, and performs coordinate conversion of the sectional image frame data in accordance with the image displaying unit 128.

The sectional image frame memory 118 stores at least one volume of the sectional image frame data output from the monochrome scan converter 109. At this point, pressing position information is obtained from the pressing control unit 111, and at all the scan positions in the short axis direction in the volume, selects and saves the frame at the same pressurized position from the frames during pressurization. The pressurized position can be arbitrarily specified.

The sectional image coordinate converting unit 121 performs coordinate conversion in which one volume of sectional frame data is re-placed in accordance with the movement amount in the short axis direction to produce three-dimensional volume data of the sectional image. The produced three-dimensional volume data is stored in the sectional image frame memory 118.

The volume rendering unit 124 performs one of volume rendering, maximum value projection, minimum value projection, and averaging on the volume data present in the direction of line of sight toward each pixel on the two-dimensional projection plane to produce a three-dimensional image.

For example, the volume rendering unit 124 performs the volume rendering of the three-dimensional volume data produced by the sectional image coordinate converting unit 121 based on the intensity and the opacity using the following expressions (1) to (3) to constitute the three-dimensional image of the part to be diagnosed of the object (two-dimensional projection image of three-dimensional volume data). The projection direction (direction of line of sight) is received by the operation unit 129 from the operator.

$$C\text{out}(i) = C\text{out}(i-1) + (1 - A\text{out}(i-1)) \cdot A(i) \cdot C(i) \cdot S(i) \quad \text{expression (1)}$$

$$A\text{out}(i) = A\text{out}(i-1) + (1 - A\text{out}(i-1)) \cdot A(i) \quad \text{expression (2)}$$

$$A(i) = B\text{opacity}[C(i)] \quad \text{expression (3)}$$

In the expression (1), Cout(i) represents the value output as the pixel value of the two-dimensional projection plane. C(i) represents the intensity value of an ith voxel (where i=0 to N−1) present on the line of sight when the three-dimensional image is viewed from a certain point on the two-dimensional projection plane. The voxel refers to the position of each of intensity data items constituting the three-dimensional volume data. When N voxels are arranged on the line of sight, the intensity value Cout(N−1) calculated by accumulating the intensity values of the voxels (i=0 to N−1) with the expression (1) is the pixel value to be output finally. Cout(i−1) represents the accumulated value up to an i−1th voxel.

A(i) in the expression (1) represents the opacity of the ith voxel present on the line of sight and takes values ranging from 0 to 1.0. The opacity A(i) is determined in accordance with the magnitude of the intensity value of the voxel by referencing a table (Bopacity[C(i)]) defining the predefined relationship between intensity value C(i) and opacity or by substituting the intensity value C(i) into a function (Bopacity [C(i)]) defining the predefined relationship between the intensity value C(i) and opacity as shown in the expression (3). For example, a higher opacity is provided for a voxel having a higher intensity value. The opacity thus provided in accordance with the intensity value determines the contribution of the intensity value C(i) of the voxel to the intensity value Cout(N−1) of the two-dimensional projection plane to be output.

Aout(i) in the expression (2) is the value calculated by accumulating the opacities A(i) provided from the expression (3) in accordance with the right side of the expression (2) up to the ith voxel. In the expression (1), the accumulated value Aout(i−1) of the opacities up to the i−1th voxel calculated as in the expression (2) is used. As apparent from the expression (2), Aout (i) is accumulated each time the voxel is passed, and is converged to 1.0. Thus, when the accumulated value Aout (i−1) of the opacities up to the i−1th voxel is approximately 1.0 as shown in the above expression (1), the second term in the right side of the expression (1) is 0, and the intensity value C(i) of the ith and subsequent voxels is not reflected in the two-dimensional projection image (three-dimensional) to be output. The initial values of Cout(i) and Aout(i) are zero.

S(i) in the expression (1) is a weight component for shading and is calculated from the slope of the intensity value determined from the intensity value C(i) and its surrounding intensity values. For example, when the normal to the plane centered on the ith voxel (slope of the intensity value) matches the optical axis of a predefined light source, the light is reflected most strongly and thus 1.0 is provided as S(i) for the voxel i based on a predefined table and function. When the light source is orthogonal to the normal, 0.0 is provided as S(i). This provides the shading for the obtained two-dimensional projection image to achieve a highlighting effect.

The arbitrary cross-section sectional image constituting unit 120 reads the volume data in the sectional image frame memory 118 to produce a sectional image (sectional MPR image) of an arbitrary cross section. A plurality of positions can be set for the arbitrary cross section, and the arbitrary cross-section sectional image constituting unit 120 produces a monochrome sectional image for each of the plurality of arbitrary cross-section positions. The position and the number of the arbitrary cross sections (the number of sectional images to be produced) are received by the operation unit 129 from the operator and are set in the arbitrary cross-section sectional image constituting unit 120.

The RF frame data selecting unit 113 stores a plurality of RF signal frame data items from the phasing and adding unit 107 and selects a set, that is, two RF signal frame data items from the stored group of RF signal frame data items. For example, the RF signal frame data produced on the time series, that is, on the basis of the frame rate of the image from the phasing and adding unit 107 is sequentially stored in the RF frame data selecting unit 113, the stored RF signal frame data (N) is selected as first data and one RF signal frame data (X) is selected from a group of RF signal frame data items (N−1, N−2, N−3, ... N−M) stored previously at the same time. N, M, and X represent index numbers provided for the RF signal frame data items and are natural numbers.

The displacement measuring unit 114 performs one-dimensional or two-dimensional correlation processing on the selected set of data items, that is, the RF signal frame data (N) and the RF signal frame data (X) to determine one-dimensional or two-dimensional displacement distribution for a displacement and a movement vector, that is, the direction and the magnitude of displacement in the living organ for each point in the sectional image. A block matching method is used for detecting the movement vector. The block matching method includes dividing the image into blocks each constituting of N pixels by N pixels, for example, focusing on a block within an area of interest, searching the previous frame for a block most approximate to the focused block, and referencing that block to determine a sample value through predictive coding, that is, differences.

The elasticity information calculating unit 115 performs predetermined calculations based on the movement vector output from the displacement measuring unit 114 to calculate the elasticity value of the living organ for each point in the sectional image and produces an elasticity image signal based on the elasticity value, that is, elasticity frame data. The elasticity value mentioned herein may be a value representing the elasticity of the organ of the object 102, and examples thereof include strain, coefficient of elasticity, displacement, viscosity, strain ratio and the like.

For example, the data about the strain is calculated by spatial differentiation of the movement amount of the living organ such as the displacement. The data of the coefficient of elasticity is calculated by dividing the change in pressure output from the pressure measuring unit 110 by the change in strain. For example, when L(X) represents the displacement measured by the displacement measuring unit 114 and P(X) represents the pressure measured by the pressure measuring unit 121, the strain $\Delta S(X)$ can be calculated by spatial differentiation of L(X) and thus can be determined by using the expression $\Delta S(X) = \Delta L(X)/\Delta X$, The Young's modulus Ym(X) of the data of the coefficient of elasticity is calculated with the expression $Ym = (\Delta P(X))/\Delta S(X)$. Since the coefficient of elasticity of the living organ for each point in the sectional image is determined from the Young's modulus Ym, two-dimensional elasticity image data can be obtained successively. The Young's modulus refers to a ratio between the simple tensile stress applied to a substance and the strain caused in parallel with the tension.

The elasticity image constituting unit 116 performs image processing on the elasticity frame data output on the time series from the elasticity information calculating unit 115. The elasticity image scan converter 117 is formed of a coordinate converter, a frame memory, and a controller, and stores the output from the elasticity information calculating unit 115 in the frame memory. The elasticity image scan converter 117 reads the elasticity image frame data stored in the frame memory as a single image in synchronization and performs coordinate conversion of that frame data in accordance with the image displaying unit 128.

At least one volume of the color elasticity image frame data output from the elasticity image scan converter 117 is stored in the elasticity image frame memory 119. The elasticity image coordinate converting unit 123 performs coordinate conversion in which one volume of elasticity frame data is re-placed in accordance with the movement amount in the short axis direction to produce three-dimensional volume data of the elasticity image.

The volume rendering unit 125 performs one of volume rendering, maximum value projection, minimum value projection, and averaging on the volume data present in the direction of line of sight toward each pixel on the two-dimensional projection plane to produce three-dimensional elasticity image.

For example, the volume rendering unit 42 performs the volume rendering of the elasticity image three-dimensional volume data based on the elasticity value and the opacity using the following expressions (4) to (6). The projection direction (direction of line of sight) is received by the operation unit 129 from the operator.

$$E\text{out}(i) = E\text{out}(i-1) + (1 - A\text{out}(i-1)) \cdot A(i) \cdot E(i) \cdot S(i) \quad \text{expression (4)}$$

$$A\text{out}(i) = A\text{out}(i-1) + (1 - A\text{out}(i-1)) \cdot A(i) \quad \text{expression (5)}$$

$$A(i) = E\text{opacity}[C(i)] \quad \text{expression (6)}$$

In the expression (4), $E\text{out}(i)$ represents the value output as the pixel value of the projection plane. $E(i)$ represents the elasticity value of an ith voxel (where $i=0$ to $N-1$) present on the line of sight when the three-dimensional elasticity image is viewed from a certain point on the two-dimensional projection plane. When the elasticity values of N voxels are arranged on the line of sight, the accumulated value $E\text{out}(N-1)$ calculated by accumulating the elasticity values ($i=0$ to $N-1$) with the expression (4) is the pixel value to be output finally. $E\text{out}(i-1)$ represents the accumulated value up to the i-1th voxel.

$A(i)$ in the expression (4) represents the opacity of the ith voxel present on the line of sight and takes values ranging from 0 to 1.0. The opacity $A(i)$ is determined in accordance with the magnitude of the elasticity value of the voxel by referencing a table ($E\text{opacity}[E(i)]$) defining the predefined relationship between elasticity value $E(i)$ and opacity or by substituting the elasticity value $E(i)$ into a function ($E\text{opacity}[E(i)]$) defining the predefined relationship between the elasticity value $E(i)$ and opacity as shown in the expression (6).

$A\text{out}(i)$ in the expression (5) is the value calculated by accumulating the opacities $A(i)$ provided from the expression (6) in accordance with the right side of the expression (5) up to the ith voxel. In the expression (4), the accumulated value $A\text{out}(i-1)$ of the opacities up to the i-1th voxel calculated as in the expression (5) is used. As apparent from the expression (5), $A\text{out}(i)$ is accumulated each time the voxel is passed, and is converged to 1.0. Thus, when the accumulated value $A\text{out}(i-1)$ of the opacities up to the i-1th voxel is approximately 1.0 as shown in the above expression (4), the second term in the right side of the expression (4) is 0, and the elasticity value $E(i)$ of the ith and subsequent voxels is not reflected in the two-dimensional projection image (three-dimensional) to be output. The initial values of $E\text{out}(i)$ and $A\text{out}(i)$ are zero.

$S(i)$ in the expression (4) is a weight component for shading and is calculated from the slope of the elasticity value determined from the elasticity value $E(i)$ and its surrounding elasticity values. For example, when the normal to the plane centered on the ith voxel (slope of the elasticity value) matches the optical axis of a predefined light source, the light is reflected most strongly and thus 1.0 is provided as $S(i)$ for the voxel i based on a predefined table and function. When the light source is orthogonal to the normal, 0.0 is provided as $S(i)$. This provides the shading for the obtained two-dimensional projection image to achieve a highlighting effect.

The arbitrary cross-section elasticity image constituting unit 122 cuts an arbitrary cross section from the elasticity image volume data stored in the elasticity image frame memory 119 and outputs a two-dimensional elasticity image (elasticity MPR image) of the arbitrary cross section. A plurality of positions can be set for the arbitrary cross section, and the arbitrary cross-section sectional image constituting unit 122 produces a two-dimensional elasticity image for each of the plurality of arbitrary cross-section positions. The position and the number of the arbitrary cross sections (the number of two-dimensional elasticity images to be produced) are received by the operation unit 129 from the operator and is set in the arbitrary cross-section elasticity image constituting unit 122.

Figure 2:
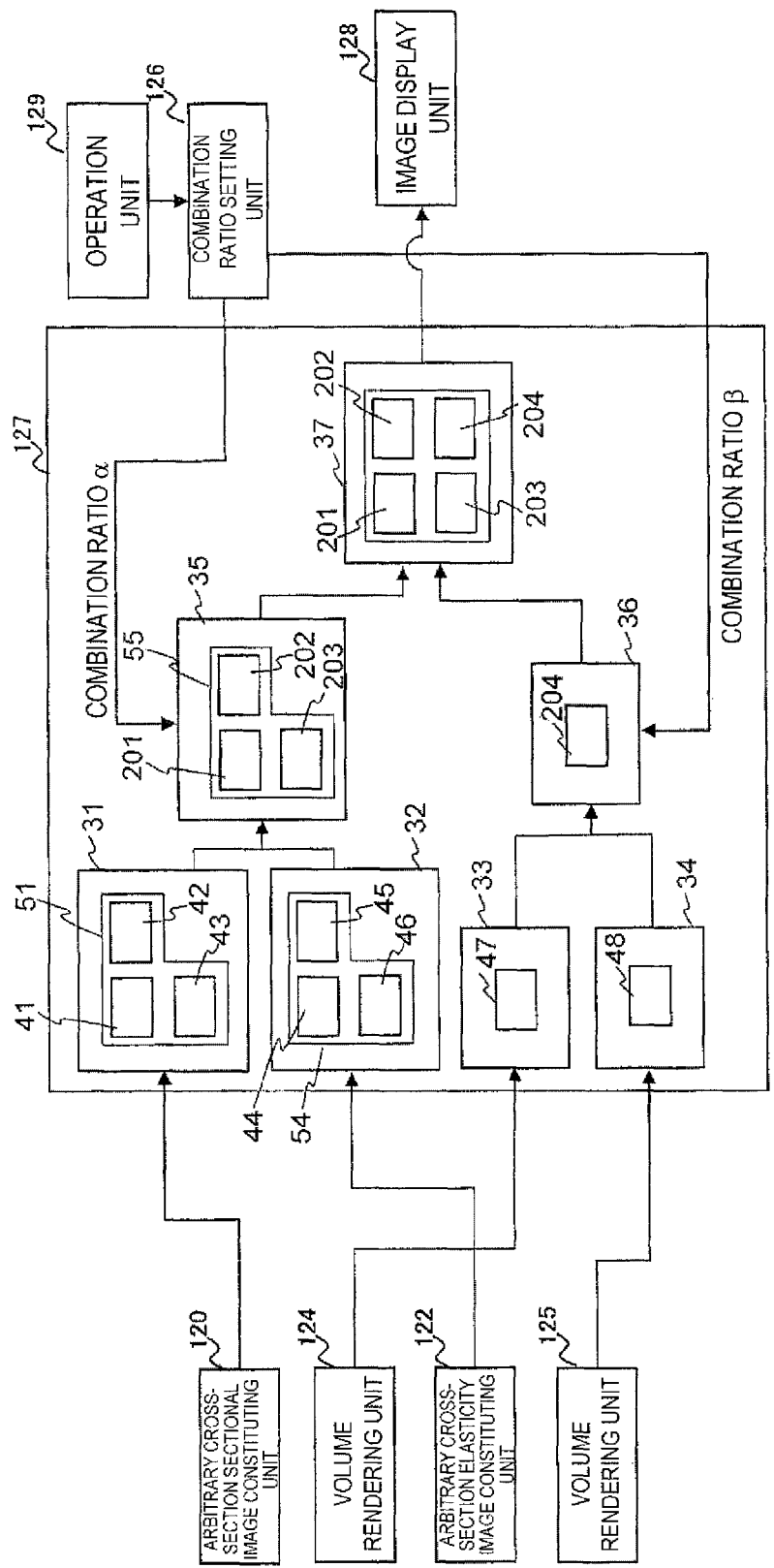
FIG. 2 A block diagram showing the detailed configuration of a combined image processing unit 127 of the apparatus in FIG. 1.

Next, the combined image processing unit 127 is described in detail with reference to FIG. 2. As shown in FIG. 2, the combined image processing unit 127 includes a sectional MPR color converting unit 31, an elasticity MPR color converting unit 32, a three-dimensional image color converting unit 33, a three-dimensional elasticity image color converting unit 34, an MPR image combining unit 35, a three-dimensional image combining unit 36, and a parallel placing unit 37. In practice, the combined image processing unit 127 has a CPU and a memory, in which the CPU reads a program stored in the memory to perform color conversion processing and combination processing shown in a flow of FIG. 3 and stores the results in a predetermined area of the memory as required, thereby realizing the operation of each of the units.

The sectional MPR color converting unit 31 receives one or more arbitrary cross-section sectional images (sectional MPR images) produced by the arbitrary cross-section sectional image constituting unit 120 and performs RGB color conversion thereof (step 61) Specifically, since the sectional MPR image produced by the arbitrary cross-section sectional image constituting unit 120 is a monochrome image having pixel values representing intensity information, the image is converted into a color sectional image in order to perform superimposition on a two-dimensional elasticity image which is a color image.

Description is made herein with an example in which the arbitrary cross-section sectional image constituting unit 120 produces sectional images 41, 42, and 43 of three orthogonal cross sections at an arbitrary position set by the operator. The sectional images 41, 42, and 43 of the three orthogonal cross sections are passed from the arbitrary cross-section Sectional image constituting unit 120 to the sectional MPR color converting unit 31 as a single image 51 including those images placed in a predetermined arrangement as shown in FIG. 2. Since it is only required to perform the color conversion processing on the single image 51, the color conversion processing can be performed quickly.

The sectional MPR color converting unit 31 performs conversion as in the following expressions (7) to (9) where $C_{MPR}$ (x, y) represents the intensity value of a pixel at position x, y in the sectional MPR image 51 received from the arbitrary cross-section sectional image constituting unit 120, $C_{MPR}$(R) (x, y), $C_{MPR}$(G) (x, y), and $C_{MPR}$(B) (x, y) represent the pixel output values of red (R), green (G), and blue (B) after the color conversion, respectively. The image 51 after the color conversion is stored in a predetermined area of the memory within the combined image processing unit 127.

$$C_{MPR}(R)(x,y)=C_{MPR}(x,y) \quad \text{expression (7)}$$

$$C_{MPR}(G)(x,y)=C_{MPR}(x,y) \quad \text{expression (8)}$$

$$C_{MPR}(B)(x,y)=C_{MPR}(x,y) \quad \text{expression (9)}$$

The elasticity MPR color converting unit 32 receives the elasticity value $E_{MPR}$(x, y) of the position x, y in the two-dimensional elasticity images (elasticity MPR images) 44, 45, and 46 of the three orthogonal cross sections produced by the arbitrary cross-section elasticity image constituting unit 122 and references a color map for the elasticity MPR image to produce a color image with the following expressions (10) to (12) (step 62). The color map is a table which previously defines the relationship between the value of $E_{MPR}$(x, y) and the corresponding pixel output values $E_{MPR}$(R) (x, y), $E_{MPR}$(G) (x, y), and $E_{MPR}$(B) (x, y) of red (R), green (G), and blue (B), and is referenced to determine the pixel output values $E_{MPR}$(R) (x, y), $E_{MPR}$(G) (x, y), and $E_{MPR}$(B) (x, y) with the expressions (10) to (12).

The two-dimensional elasticity images (elasticity MPR images) 44, 45, and 46 of the three orthogonal cross sections are the elasticity images of the same cross sections as the sectional images (sectional MPR images) 41, 42 and 43 of the three orthogonal cross sections. In this case, the three two-dimensional elasticity images (elasticity MPR images) 44, 45, and 46 are passed from the arbitrary cross-section elasticity image constituting unit 122 to the elasticity MPR color converting unit 32 as a single image 54 including those images placed in the same arrangement as the image 51 before processing.

$$E_{MPR}(R)(x,y)=ET_{MPR}(R)[E_{MPR}(x,y)] \quad \text{expression (10)}$$

$$E_{MPR}(G)(x,y)=ET_{MPR}(G)[E_{MPR}(x,y)] \quad \text{expression (11)}$$

$$E_{MPR}(B)(x,y)=ET_{MPR}(B)[E_{MPR}(x,y)] \quad \text{expression (12)}$$

$ET_{MPR}$(R): table data (for R value) of color map for elasticity MPR image
$ET_{MPR}$(G): table data (for G value) of color map for elasticity MPR image
$ET_{MPR}$(B): table data (for B value) of color map for elasticity MPR image The three-dimensional image color converting unit 33 receives the pixel values Cout(x, y) of the position x, y in the three-dimensional image 47 produced with the expressions (1) to (3) from the sectional image volume data by the volume rendering unit 124 and references a color map for the three-dimensional image with the following expressions (13) to (15) to perform conversion into a color image (step 63). The color map is a table which previously defines the relationship between the value of Cout(x, y) and the corresponding pixel output values $Cout_{3D}$(R) (x, y), $Cout_{3D}$(G) (x, y), and $Cout_{3D}$(B) (x, y) of red (R), green (G), and blue (B), and is referenced to determine the pixel output values $Cout_{3D}$(R) (x, y), $Cout_{3D}$(G) (x, y), and $Cout_{3D}$(B) (x, y) of the three-dimensional image 47 with the expressions (13) to (15).

$$Cout_{3D}(R)(x,y)=CT_{3D}(R)[Cout(x,y)] \quad \text{expression (13)}$$

$$Cout_{3D}(G)(x,y)=CT_{3D}(G)[Cout(x,y)] \quad \text{expression (14)}$$

$$Cout_{3D}(B)(x,y)=CT_{3D}(B)[Cout(x,y)] \quad \text{expression (15)}$$

$CT_{3D}$(R): table data (for R value) of color map for three-dimensional image
$CT_{3D}$(G): table data (for G value) of color map for three-dimensional image
$CT_{3D}$(B): table data (for B value) of color map for three-dimensional image The three-dimensional elasticity image color converting unit 34 receives the pixel values Eout(x, y) of the position x, y in the three-dimensional elasticity images 48 produced with the expressions (4) to (6) from the elasticity image volume data by the volume rendering unit 125 and references a color map for the three-dimensional elasticity image with the following expressions (16) to (18) to produce a color three-dimensional elasticity image 48 (step 64). The color map is a table which previously defines the relationship between the value of Eout(x, y) and the corresponding pixel output values $Eout_{3D}$(R) (x, y), $Eout_{3D}$(G) (x, y), and $Eout_{3D}$(B) (x, y) of red (R), green (G), and blue (B), and is referenced to determine the pixel output values $Eout_{3D}$(R) (x, y), $Eout_{3D}$(G) (x, y), and $Eout_{3D}$(B) (x, y) of the three-dimensional elasticity image 48 with the expressions (16) to (18).

$$Eout_{3D}(R)(x,y)=ET_{3D}(R)[Eout(x,y)] \quad \text{expression (16)}$$

$$Eout_{3D}(G)(x,y)=ET_{3D}(G)[Eout(x,y)] \quad \text{expression (17)}$$

$$Eout_{3D}(B)(x,y)=ET_{3D}(B)[Eout(x,y)] \quad \text{expression (18)}$$

Figure 4:
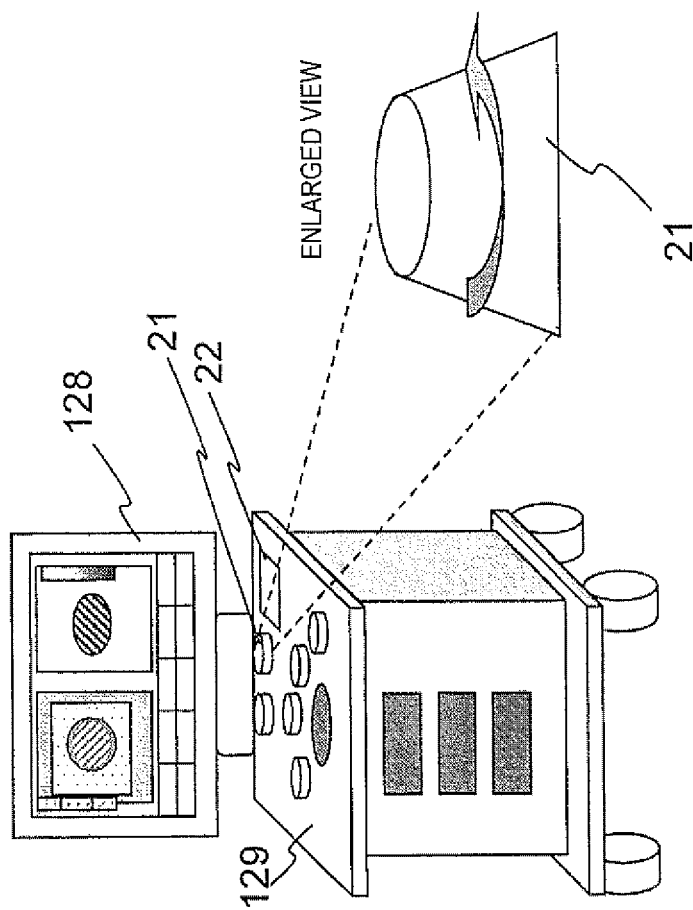
FIG. 4 A perspective view showing an operation panel of an operation unit 129 of the apparatus in FIG. 1 and a perspective enlarged view of a toggle switch 21.
Figure 5:
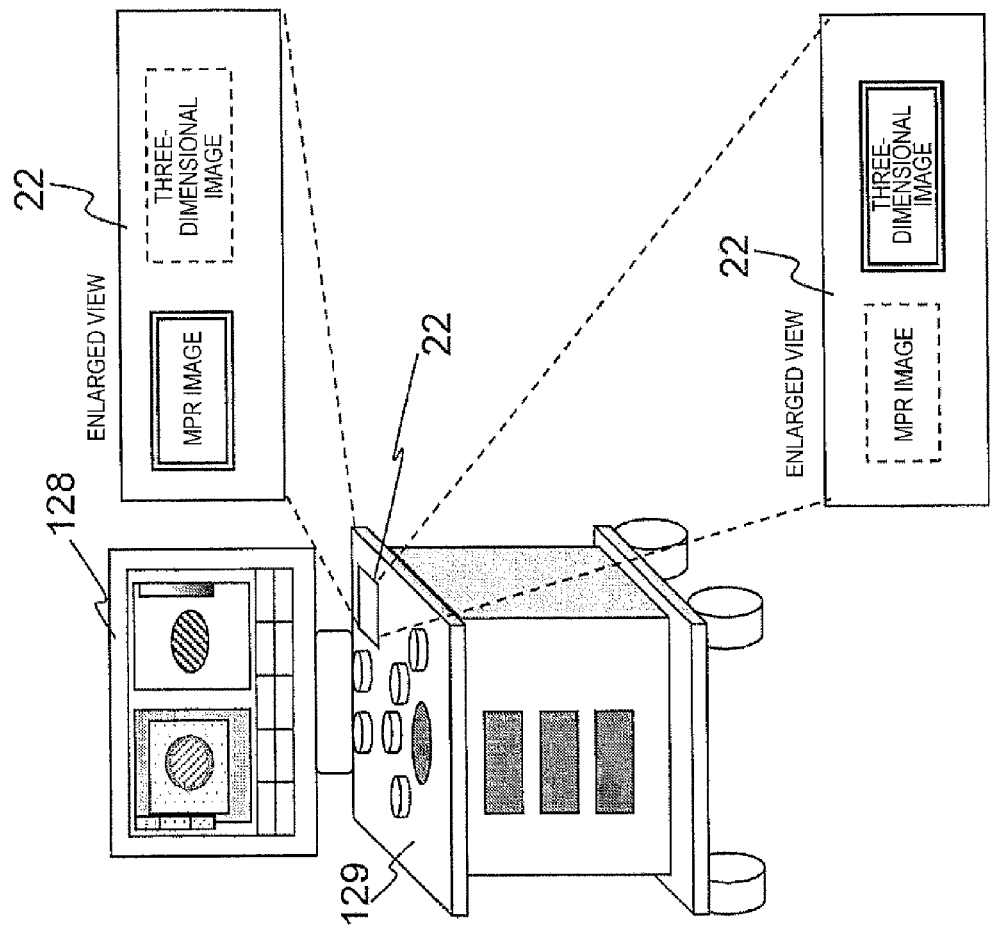
FIG. 5 A perspective view showing the operation panel of the operation unit 129 of the apparatus in FIG. 1 and an enlarged view of an MPR image/three-dimensional image selecting switch.

$ET_{3D}$(R): table data (for R value) of color map for three-dimensional elasticity image
$ET_{3D}$(G): table data (for G value) of color map for three-dimensional elasticity image
$ET_{3D}$(B): table data (for B value) of color map for three-dimensional elasticity image The operation unit 129 includes an operation panel placed under the image display unit 128 as shown in FIG. 4. The operation panel includes a toggle switch 21 for setting the combination ratio and an MPR image/three-dimensional image selecting switch 22. The MPR image/three-dimensional image selecting switch 22 has the configuration as shown in FIG. 5, and when a button labeled with "MPR image" is selected, the combination ratio setting unit 126 sets a value α set by the toggle switch 21 in the MPR image combining unit 35. On the other hand, when a button labeled with "three-dimensional image" is selected, the combination ratio setting unit 126 sets a value β set by the toggle switch 21 in the three-dimensional image combining unit 36. This allows the operator to easily set the desired combination ratios α and β through the operation of the MPR image/three-dimensional image selecting switch 22 and the operation of the toggle switch 21.

The MPR image combining unit 35 adds the sectional MPR image 51 to the elasticity MPR image 54 to produce an MPR combined image 55 (step 65). At this point, the combination ratio α for use is received by the operation unit 29 from the operator and is set by the combination ratio setting unit 126 in the MPR image combining unit 35. Specifically, the color pixel output values $C_{MPR}$(R) (x, y), $C_{MPR}$(G) (x, y) and $C_{MPR}$(B) (x, y) after the conversion in the sectional MPR color converting unit 31 are combined with the color pixel output values $E_{MPR}$(R) (x, y) $E_{MPR}$(G) (x, y), and $E_{MPR}$(B) (x, y) after the conversion in the elasticity MPR color converting unit 32 with the following expressions (19) to (21) to determine the pixel values $D_{MPR}(R)(x, y)$, $D_{MPR}(G)(x, y)$, and $D_{MPR}(B)(x, y)$ in the MPR combined image 55.

$$D_{MPR}(R)(x,y)=(1-\alpha)\times E_{MPR}(R)(x,y)+\alpha\times C_{MPR}(R)(x,y) \quad (19)$$

$$D_{MPR}(G)(x,y)=(1-\alpha)\times E_{MPR}(G)(x,y)+\alpha\times C_{MPR}(G)(x,y) \quad (20)$$

$$D_{MPR}(B)(x,y)=(1-\alpha)\times E_{MPR}(B)(x,y)+\alpha\times C_{MPR}(B)(x,y) \quad (21)$$

Figure 6:
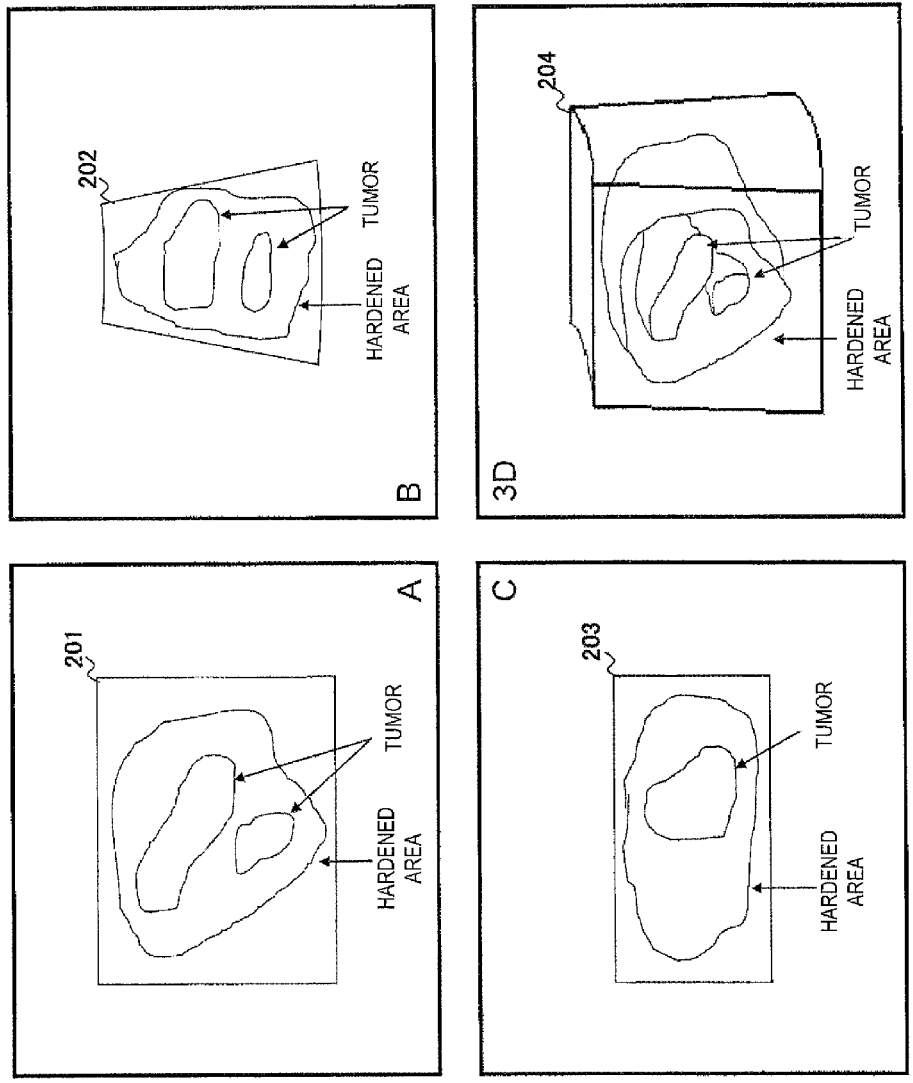
FIG. 6 An explanatory view showing an example of combined images in Embodiment 1.

Since the sectional MPR image 51 is provided by placing the sectional images 41, 42, and 43 of the three orthogonal cross sections in the predetermined arrangement, and the elasticity MPR image 54 is provided by placing the elasticity images 44, 45, and 46 of the corresponding three orthogonal cross sections in the same arrangement, the combination with the above expressions (19) to (21) is performed to result in MPR combined images 201, 202, and 203 of the three orthogonal cross sections provided by adding the sectional MPR image 51 of the three orthogonal cross sections at the ratio $\alpha$ to the elasticity MPR image 54 of the corresponding three orthogonal cross sections at the ratio $(1-\alpha)$ (see FIG. 6).

Similarly, the three-dimensional image combining unit 36 adds the color-converted three-dimensional image 47 to the color-converted three-dimensional elasticity image 48 to produce a three-dimensional combined image 204 (step 66). At this point, the combination ratio $\beta$ received by the operation unit 129 from the operator and set by the combination ratio setting unit 126 in the three-dimensional image combining unit 36 is used. Specifically, the color pixel output values $Cout_{3D}(R)(x, y)$ $Cout_{3D}(G)(x, y)$, and $Cout_{3D}(B)(x, y)$ after the conversion in the three-dimensional image color converting unit 33 are combined with the color pixel output values $Eout_{3D}(R)(x, y)$, $Eout_{3D}(G)(x, y)$ and $Eout_{3D}(B)(x, y)$ after the conversion in the three-dimensional elasticity image color converting unit 34 with the following expressions (22) to (24) to determine the pixel values $D_{3D}(R)(x, y)$, $D_{3D}(G)(x, y)$, and $D_{3D}(B)(x, y)$ in the three-dimensional combined image 204.

$$D_{3D}(R)(x,y)=(1-\beta)\times Eout_{3D}(R)(x,y)+\beta\times Cout_{3D}(R)(x,y) \quad (22)$$

$$D_{3D}(G)(x,y)=(1-\beta)\times Eout_{3D}(G)(x,y)+\beta\times Cout_{3D}(G)(x,y) \quad (23)$$

$$D_{3D}(B)(x,y)=(1-\beta)\times Eout_{3D}(B)(x,y)+\beta\times Cout_{3D}(B)(x,y) \quad (24)$$

The combination with the above expressions (22) to (24) is performed to result in the three-dimensional combined image 204 provided by adding the three-dimensional image at the ratio $\beta$ and the three-dimensional elasticity image at the ratio $(1-\beta)$ (see FIG. 6).

The parallel placing unit 37 produces the image including the obtained MPR combined image 55 and three-dimensional combined image 204 placed in parallel and causes the image display unit 128 to display that image as shown in FIG. 6 (steps 67 and 68).

As shown in FIG. 6, in the present embodiment, the combined images 201 to 203 provided by combining the sectional MPR image and the elasticity MPR image at the combination ratio $\alpha$ set by the operator and the combined image 204 provided by combining the three-dimensional image and the three-dimensional elasticity image at the combination ratio $\beta$ are displayed in parallel at the same time. Since both a tumor and a hardened area are displayed in each of the MPR combined images 201 to 203 of the three orthogonal cross sections in FIG. 6, the organ structure around the tumor and the hardness information can be easily recognized to perform an efficient diagnosis. In the three-dimensional combined image 204 of the three-dimensional image and the three-dimensional elasticity image, both a tumor and a hardened area are also displayed. This is because the operator arbitrarily sets the different and optimal combination ratios $\alpha$ and $\beta$. Thus, the operator can contrast the organ structure with the hardness information in the three-dimensional combined image 204 to locate the position where the operator wishes to see the inside more, and the operator can contrast the inside organ structure with the hardness information in the MPR combined images 201 to 203 to perform a diagnosis.

Figure 7:
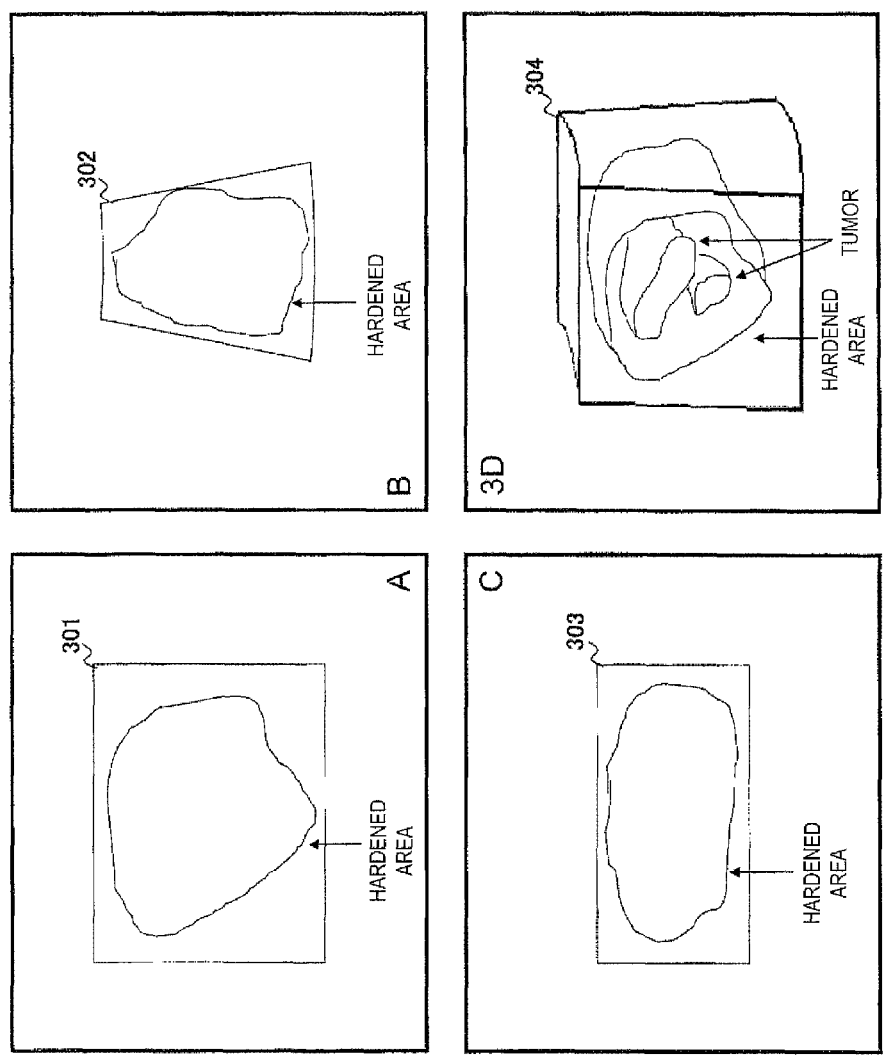
FIG. 7 An explanatory view showing an example of combined images in a comparative example.

FIG. 7 shows a comparative example in which combined images 301 to 304 are provided by setting the same predefined fixed value as the combination ratio of the sectional MPR image and the elasticity MPR image and the combination ratio of the three-dimensional image and the three-dimensional elasticity image. The combined image 304 of the three-dimensional image and the three-dimensional elasticity image shows both a tumor and a hardened area. In the combined images 301 to 304 of the sectional MPR images and the elasticity MPR images of the three orthogonal cross sections, however, a tumor is overwritten with a hardened area to make it difficult to perform a diagnosis while the operator contrasts the organ structure with the hardness information.

While the present embodiment has been described with the example where the toggle switch and the selecting button are used in the operation panel of the operation unit 129, the present invention is not limited thereto, and the operator may use a trackball or an encoder button to determine the combination ratio.

Embodiment 2

Embodiment 2 is described with reference to FIG. 8. Embodiment 2 differs from Embodiment 1 in that indicators 405 and 406 showing the setting values of combination ratios $\alpha$ and $\beta$ are displayed and changeable in synchronization. In the following, only the configuration different from that in Embodiment 1 is described, and the description of the configuration similar to that in Embodiment 1 is omitted.

The indicator 405 showing the combination ratio $\alpha$ of MPR combined images 201 to 203 of three orthogonal cross sections is displayed in one of those images, and the indicator 406 showing the combination ratio $\beta$ is displayed in the three-dimensional image combined image 204. The images of the indicators 405 and 406 are produced and displayed by the combined image processing unit 127.

When the operator uses the operation unit 129 to set the combination ratios $\alpha$ and $\beta$, the combined image processing unit 127 sets and updates the combination ratios $\alpha$ and $\beta$ in the MPR image combining unit 35 and the three-dimensional image combining unit 36 as described in Embodiment 1, and updates the display such that the combination ratio $\alpha$ is displayed in the indicator 405 and the combination ratio $\beta$ is displayed in the indicator 406.

This allows the operator to easily see the setting status of the combination ratios by visually recognizing the indicators 405 and 406. The operator can visually recognize the displayed MPR combined images 201 to 204 and three-dimensional image combined image 204, and can change the combination ratios $\alpha$ and $\beta$ as required to change into the combined image on which the desired organ structure or organ elasticity information are easily checked. Thus, an efficient diagnosis can be performed.

The combined image processing unit 127 may change the combination ratio $\alpha$ and the combination ratio $\beta$ in synchronization. The initial values $\alpha$ and $\beta$ appropriate for the combination ratios of the MPR combined images 201 to 204 and the three-dimensional image combined image 204 are previously determined through experiments or the like. Before the setting of the combination ratios $\alpha$ and $\beta$ is received from the operator through the operation unit 129, the MPR combined images 201 to 204 and the three-dimensional image combined image 204 are displayed at the combination ratios α and β of the initial values, and the indicators 405 and 406 showing the combination ratios α and β, respectively, are displayed. When the operator selects the synchronization setting of the combination ratios α and β through the operation unit 129, and if the operator changes one of the values of the combination ratios α and β, then the combined image processing unit 127 changes the other combination ratio in synchronization therewith. This synchronization is performed so as to maintain the difference between the combination ratios α and β of the initial values. For example, when the operator changes the combination ratio α into α+s, the combination ratio β is changed into β+s in synchronization.

The synchronization of the combination ratios α and β can change the appearance of the organ structure information and the elasticity information synchronously in the MPR combined images 201 to 203 and the three-dimensional image combined image 204 to find the optimal combination ratio efficiently.

The indicators 405 and 406 may be provided by using a progress bar, a numeric value, or a color.

Embodiment 3

An ultrasonic diagnostic apparatus according to Embodiment 3 is described with reference to FIG. 9. The ultrasonic diagnostic apparatus according to Embodiment 3 differs from Embodiment 1 in that individual combination ratios can be set in MPR combined images 201 to 204 of a plurality of cross sections. Since the other configuration is similar to that in Embodiment 1, the description thereof is omitted.

The operation of the ultrasonic diagnostic apparatus according to Embodiment 3 is described. The operation unit 129 further includes a selecting button, not shown, for selecting one of a plurality of MPR images 201, 202, and 203. The operator uses the selecting button in the operation unit 129, the MPR image/three-dimensional image selecting switch 22, and the toggle switch 22 to individually set the combination ratios α1, α2, and α3 of the plurality of MPR combined images 201, 202, and 203, and the combination ratio β of the three-dimensional combined image 204. The combination ratio setting unit 126 sets the combination ratios α1, α2, and α3 in the MPR image combination unit 35 and sets the combination ratio β in the three-dimensional image combining unit 36.

Figure 3:
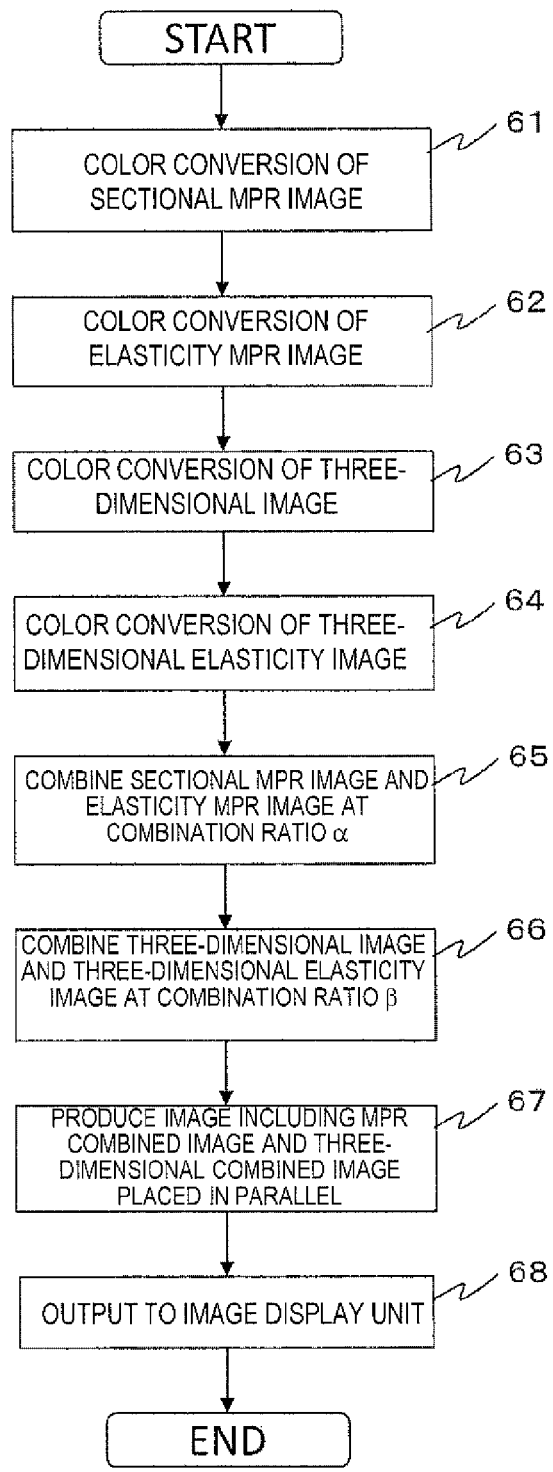
FIG. 3 A flow chart showing the operation of the combined image processing unit 127 of the apparatus in FIG. 1.

The sectional MPR color converting unit 31 sequentially receives the sectional MPR images 41, 42, and 43 of the three orthogonal cross sections from the arbitrary cross-section sectional image constituting unit 120 and repeats step 61 in FIG. 3 to perform color conversion of the sectional MPR images 41, 42, and 43. Similarly, the elasticity MPR color converting unit 32 sequentially receives the elasticity MPR images 44, 45, and 46 of the three orthogonal cross sections from the arbitrary cross-section elasticity image constituting unit 122 and repeats step 62 in FIG. 3 three times to produce the color images of the sectional MPR images 44, 45, and 46.

The MPR image combining unit 35 repeats step 65 in FIG. 3 three times with the set combination ratios α1, α2, and α3 to produce the MPR combined images 201, 202, and 203 at the combination ratios α1, α2, and α3. The other steps are similar to those in Embodiment 1.

For changing the combination ratio, the operator uses the selecting switch of the operation unit 129 to select a cross section of the MPR image the combination ratio of which is wished to be changed, and sets the combination ratio with the toggle switch 21. The combination ratio setting unit 126 sets the changed combination ratio in the MPR image combining unit 35. This can display the MPR combined image having the changed combination ratio of the selected MPR image in the image display unit 128.

In Embodiment 3, the combination ratio of the selected MPR cross section can be changed to display the combined image including the highlighted sectional image or elasticity image, thereby providing the organ structure and hardness information in detail.

For example, FIG. 9 shows an example in which the only one MPR combined image 201 of the MPR combined images 201 to 203 is combined at a combination ratio different from the others. Since the MPR combined image 201 includes the highlighted elasticity MPR image unlike the other MPR combined images 202 and 203, the hardened area is highlighted.

Since the other MPR combined images 202 and 203, and the three-dimensional combined image 204 have the combination ratios at which both the elasticity MPR image and the sectional MPR image can be recognized, both the organ structure around the tumor and the hardened area can be seen. The highlighting of the elasticity MPR image, for example, allows the recognition of the elasticity information only on the cross section desired by the operator, and the organ structure can be recognized in the other MPR combined images, so that the information about the object can be checked in desired conditions.

Embodiment 4

An ultrasonic diagnostic apparatus according to Embodiment 4 is described with reference to FIG. 10. Similarly to the apparatus of Embodiment 3, the apparatus of Embodiment 4 enables setting of individual combination ratios in MPR combined images 602 to 610 of a plurality of cross sections, respectively. Embodiment 4 differs from Embodiment 3 in that the three-dimensional combined image 204 is not displayed in Embodiment 4 but only the MPR combined image is displayed and is a multi-sliced image. The multi-sliced image consists of a reference cross-section image (reference image) 601 and a plurality of parallel observation cross-section images (sliced images) 603 to 610 orthogonal to the reference cross section, and those images are displayed in parallel in Embodiment 4.

The reference image is an image of a cross section determined arbitrarily by the operator from the volume data, and one or more sliced images are set at an arbitrary position. The operator manipulates the operation unit 129 to set the positions and the numbers of the reference image and the sliced images in the arbitrary cross-section sectional image constituting unit 120 and the arbitrary cross-section elasticity image constituting unit 122. The combined image processing unit 127 performs the color conversion processing at steps 61 and 62 in FIG. 3 and the combination processing at step 65 on each of the images similarly to Embodiment 3 to display the reference image 601 and the sliced images 603 to 610 formed of the MPR combined image provided by combining the sectional MPR image and the elasticity MPR image as shown in FIG. 10.

The combination ratio $\alpha_R$ of the reference image 601 and the combination ratios $\alpha_{S1}$ to $\alpha_{S8}$ of the eight sliced images 603 to 610 are set by the operator in the operation unit 129 similarly to Embodiment 3. The combination ratio setting unit 126 sets the combination ratio $\alpha_R$ and $\alpha_{S1}$ to $\alpha_{S8}$ in the MPR image combination unit 35. The MPR image combination unit 35 performs combination processing with the combination ratios $\alpha_R$ and $\alpha_{S1}$ to $\alpha_{S8}$ set for the reference image 601 and the sliced images 603 to 610.

Slice lines 602 on the reference image 601 in FIG. 10 indicate the positions of the observation cross sections. The sliced image 607 shows a sliced image at a position indicated by a certain slice line, and includes the highlighted hardened area since the image is combined at a combination ratio different from those of the other sliced images.

The operator uses the operation unit 129 to set the combination ratio of the multi-sliced image and visually recognizes the displayed image. When the image includes a part which the operator should pay attention, and the operator wishes to see a certain sliced image at a changed combination ratio, the operator can make a selection through the operation unit 129 and change the combination ratio $\alpha_S$ as required. This operation displays the sliced image combined at the changed combination ratio.

The operation described above can display the combined image including the highlighted sectional image or elasticity image for each of the cross sections of the multi-sliced image to allow the detailed observation of the transition of the organ structure and the hardness information from one cross section to the next, thereby performing an efficient diagnosis.

In Embodiment 4, the reference image 601 may not be displayed but only the sliced images 603 to 610 may be displayed. It goes without saying that the three-dimensional combined image may be displayed together with the multi-sliced image in Embodiment 4.

DESCRIPTION OF REFERENCE NUMERALS AND SIGNS

21 TOGGLE SWITCH, 22 MPR IMAGE/THREE-DIMENSIONAL IMAGE SELECTING SWITCH, 31 SECTIONAL MPR COLOR CONVERTING UNIT, 32 ELASTICITY MPR COLOR CONVERTING UNIT, 33 DIMENSIONAL IMAGE COLOR CONVERTING UNIT, 34 THREE-DIMENSIONAL ELASTICITY IMAGE COLOR CONVERTING UNIT, 35 MPR IMAGE COMBINING UNIT, 36 THREE-DIMENSIONAL IMAGE COMBINING UNIT, 37 PARALLEL PLACING UNIT, 101 ULTRASONIC DIAGNOSTIC APPARATUS, 102 OBJECT, 103 ULTRASONIC PROBE, 104 TRANSMITTING UNIT, 105 RECEIVING UNIT, 106 TRANSMISSION/RECEPTION CONTROL UNIT, 107 PHASING AND ADDING UNIT, 108 SECTIONAL IMAGE CONSTITUTING UNIT, 109 MONOCHROME SCAN CONVERTER, 110 PRESSING MEASURING UNIT, 111 PRESSING CONTROL UNIT, 112 MOTOR CONTROL UNIT, 113 RF FRAME DATA SELECTING UNIT, 114 DISPLACEMENT MEASURING UNIT, 115 ELASTICITY INFORMATION CALCULATING UNIT, 116 ELASTICITY IMAGE CONSTITUTING UNIT, 117 ELASTICITY IMAGE SCAN CONVERTER, 118 SECTIONAL IMAGE FRAME MEMORY, 119 ELASTICITY IMAGE FRAME MEMORY, 120 ARBITRARY CROSS-SECTION SECTIONAL IMAGE CONSTITUTING UNIT, 121 SECTIONAL IMAGE COORDINATE CONVERTING UNIT, 122 ARBITRARY CROSS-SECTION ELASTICITY IMAGE CONSTITUTING UNIT, 123 ELASTICITY IMAGE COORDINATE CONVERTING UNIT, 124 VOLUME RENDERING UNIT, 125 VOLUME RENDERING UNIT, 126 COMBINATION RATIO SETTING UNIT, 127 COMBINATION IMAGE PROCESSING UNIT, 128 IMAGE DISPLAY UNIT, 129 OPERATION UNIT, 201 TO 203 MPR COMBINED IMAGE, 204 THREE-DIMENSIONAL COMBINED IMAGE, 601 REFERENCE IMAGE (MPR COMBINED IMAGE), 602 SLICE LINE, 603 TO 610 SLICED IMAGE (MPR COMBINED IMAGE)

The invention claimed is:

1. An ultrasonic diagnostic apparatus comprising:
a transmitter that transmits ultrasonic waves into an object;
a receiver that receives a signal from the object; and
a processor programmed to:
produce a sectional image for each of a plurality of arbitrary cross sections of the object based on the received signal;
process the signal to produce a two-dimensional elasticity image of an elasticity value representing elasticity for each of the plurality of arbitrary cross sections;
process the signal to produce a three-dimensional image of a predetermined part of the object;
process the signal to produce a three-dimensional elasticity image of the elasticity value of the predetermined part of the object;
receive an operation of setting a first combination ratio from an operator;
receive an operation of setting a second combination ratio from an operator;
add the sectional image and the two-dimensional elasticity image of each of the plurality of arbitrary cross sections to produce a plurality of arbitrary cross-section combined images, at least one of the sectional images and the two-dimensional elasticity images being combined at the first combination ratio;
add the three-dimensional image and the three-dimensional elasticity image at the second combination ratio to produce a three-dimensional combined image, the second combination ratio being different from the first combination ratio; and
display the arbitrary cross-section combined images and the three-dimensional combined image side by side on a display, so as to simultaneously display an external form of the object with hardness information in the three-dimensional combined image and an inside of the object with hardness information in the arbitrary cross-section combined images.

2. The ultrasonic diagnostic apparatus according to claim 1, wherein the processor is further programmed to display an indicator representing the first combination ratio and an indicator representing the second combination ratio in at least one of the arbitrary cross-section combined images and the three-dimensional combined image, respectively.

3. The ultrasonic diagnostic apparatus according to claim 1, wherein the processor is further programmed so that when it receives an operation of setting one of the first or second combination ratio from the operator, it changes the other of the first or second combination ratio in synchronization.

4. The ultrasonic diagnostic apparatus according to claim 1, wherein the processor is further programmed to produce each of the arbitrary cross-section combined images at the first combination ratio.

5. The ultrasonic diagnostic apparatus according to claim 4, wherein the processor is further programmed to:
receive a selection of one or more of the arbitrary cross-section combined images and a change of the combination ratio of the selected arbitrary cross-section combined image from the operator, and
produce the selected arbitrary cross-section combined image with the changed combination ratio.

6. The ultrasonic diagnostic apparatus according to claim 1, wherein the sectional images and two-dimensional elasticity images are produced based on volume data produced with the received signal.

7. The ultrasonic diagnostic apparatus according to claim 6, wherein the processor is further programmed to:
- receive a selection of one or more of the arbitrary cross-section combined images and a change of the combination ratio of the selected arbitrary cross-section combined image from the operator, and
- produce the selected arbitrary cross-section combined image with the changed combination ratio.

8. An ultrasonic image display method comprising the steps of:
- transmitting ultrasonic waves into an object and producing a sectional image of an arbitrary cross section of the object based on a received signal;
- processing the signal to produce a two-dimensional elasticity image of an elasticity value representing elasticity of the arbitrary cross section;
- processing the signal to produce a three-dimensional image of a predetermined part of the object;
- processing the signal to produce a three-dimensional elasticity image of the elasticity value of the predetermined part of the object;
- adding the sectional image and the two-dimensional elasticity image of the arbitrary cross section at a first combination ratio received from an operator to produce an arbitrary cross-section combined image;
- adding the three-dimensional image and the three-dimensional elasticity image of the predetermined part at a second combination ratio received from the operator to produce a three-dimensional combined image, the second combination ratio being different from the first combination ratio; and
- displaying the arbitrary cross-section combined image and the three-dimensional combined image side by side on a display, so as to simultaneously display an external form of the object with hardness information in the three-dimensional combined image and an inside of the object with hardness information in the arbitrary cross-section combined image.

* * * * *